(12) United States Patent
Sheng et al.

(10) Patent No.: US 7,231,818 B2
(45) Date of Patent: *Jun. 19, 2007

(54) DETERMINING HORIZONTAL AND VERTICAL PERMEABILITIES BY ANALYZING TWO PRETESTS IN A HORIZONTAL WELL

(75) Inventors: James J. Sheng, Katy, TX (US); Daniel T. Georgi, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/014,422

(22) Filed: Dec. 16, 2004

(65) Prior Publication Data

US 2006/0042371 A1   Mar. 2, 2006

Related U.S. Application Data

(60) Provisional application No. 60/604,552, filed on Aug. 26, 2004.

(51) Int. Cl.
*E21B 47/00* (2006.01)
(52) U.S. Cl. .................................. 73/152.05
(58) Field of Classification Search ............ 73/152.05, 73/152.06, 38, 152.03
See application file for complete search history.

(56) References Cited

U.S. PATENT DOCUMENTS

| | | | |
|---|---|---|---|
| 4,890,487 A | 1/1990 | Dussan et al. | 73/152 |
| 5,265,015 A | 11/1993 | Auzerais et al. | 364/421 |
| 5,345,820 A * | 9/1994 | Bernhardt | 73/152.18 |
| 5,377,755 A | 1/1995 | Michaels et al. | 166/264 |
| 5,703,286 A | 12/1997 | Proett et al. | 73/152.05 |
| 5,708,204 A | 1/1998 | Kasap | 73/152.52 |
| 6,062,315 A | 5/2000 | Reinhardt | 166/381 |
| 6,478,096 B1 | 11/2002 | Jones et al. | 175/50 |
| 6,640,908 B2 | 11/2003 | Jones et al. | 175/50 |
| 6,672,386 B2 | 1/2004 | Krueger et al. | 166/252.5 |
| 7,059,179 B2 * | 6/2006 | Proett et al. | 73/152.05 |
| 2003/0094040 A1 | 5/2003 | Proett et al. | 73/152.05 |
| 2005/0279161 A1 | 12/2005 | Chen et al. | 73/152.05 |

* cited by examiner

*Primary Examiner*—Robert Raevis
(74) *Attorney, Agent, or Firm*—Madan, Mossman & Sriram, P.C.

(57) ABSTRACT

In one method, the permeabilities are obtained by correcting the geometric factor derived from combining the FRA analysis and buildup analysis. In a second method, the permeabilities are obtained by combining the spherical permeability estimated from buildup analysis and the geometric skin factor obtained from history matching the probe-pressure data. In another method, horizontal and vertical permeabilities are determined by analysis of pressure drawdown made with a single probe of circular aperture in a substantially horizontal borehole at two different walls of the borehole.

27 Claims, 11 Drawing Sheets

US 7,231,818 B2

DETERMINING HORIZONTAL AND VERTICAL PERMEABILITIES BY ANALYZING TWO PRETESTS IN A HORIZONTAL WELL

CROSS-REFERENCES TO RELATED APPLICATIONS

This application claim priority from U.S. Provisional Patent Application Ser. No. 60/604,552 filed on 26 Aug. 2004, the contents of which are incorporated herein by reference.

BACKGROUND OF THE INVENTION

1. Field of the Invention

The invention is related to the field of instruments used to sample fluids contained in the pore spaces of earth formations. More specifically, the invention is related to methods of determining hydraulic properties of anisotropic earth formations by interpreting fluid pressure and flow rate measurements made by such instruments.

2. Description of the Related Art

Electric wireline formation testing instruments are used to withdraw samples of fluids contained within the pore spaces of earth formations and to make measurements of fluid pressures within the earth formations. Calculations made from these pressure measurements and measurements of the withdrawal rate can be used to assist in estimating the total fluid content within a particular earth formation.

A typical electric wireline formation testing instrument is described, for example, in U.S. Pat. No. 5,377,755 issued to Michaels et al. Electric wireline formation testing instruments are typically lowered into a wellbore penetrating the earth formations at one end of an armored electrical cable. The formation testing instrument usually comprises a tubular probe which is extended from the instrument housing and then is impressed onto the wall of the wellbore. The probe is usually sealed on its outside diameter by an elastomeric seal or packing element to exclude fluids from within the wellbore itself from entering the interior of the probe, when fluids are withdrawn from the earth formation through the probe. The probe is selectively placed in hydraulic communication, by means of various valves, with sampling chambers included in the instrument. Hydraulic lines which connect the probe to the various sample chambers can include connection to a highly accurate pressure sensor to measure the fluid pressure within the hydraulic lines. Other sensors in the instrument can make measurements related to the volume of fluid which has entered some of the sample chambers during a test of a particular earth formation. U.S. Pat. No. 6,478,096 to Jones et al. discloses a formation pressure tester that is part of a bottomhole assembly used in drilling and can make measurements while drilling (MWD).

Properties of the earth formation which can be determined using measurements made by the wireline formation testing instrument include permeability of the formation and static reservoir pressure. Permeability is determined by, among other methods, calculating a rate at which a fluid having a known viscosity moves through the pore spaces within the formation when a predetermined differential pressure is applied to the formation. As previously stated, the formation testing instrument typically includes a sensor to make measurements related to the volume of fluid entering the sample chamber, and further includes a pressure sensor which can be used to determine the fluid pressure in the hydraulic lines connecting the probe to the sample chamber. It is further possible to determine the viscosity of the fluid in the earth formation by laboratory analysis of a sample of the fluid which is recovered from the sample chamber.

The permeability of a reservoir is an important quantity to know as it is one of the important factors determining the rate at which hydrocarbons can be produced from the reservoir. Historically, two types of measurements have been used for determination of permeability. In the so-called drawdown method, a probe on a downhole tool in a borehole is set against the formation. A measured volume of fluid is then withdrawn from the formation through the probe. The test continues with a buildup period during which the pressure is monitored. The pressure measurements may continue until equilibrium pressure is reached (at the reservoir pressure). Analysis of the pressure buildup using knowledge of the volume of withdrawn fluid makes it possible to determine a permeability.

In the so-called buildup method, fluid is withdrawn from the reservoir using a probe and the flow of fluid is terminated. The subsequent buildup in pressure is measured and from analysis of the pressure, a formation permeability is determined.

U.S. Pat. No. 5,708,204 to Kasap having the same assignee as the present application and the contents of which are fully incorporated herein by reference, teaches the Fluid Rate Analysis (FRA) method in which data from a combination of drawdown and buildup measurements are used to determine a formation permeability.

The methods described above give a single value of permeability. In reality, the permeability of earth formations is anisotropic. It is not uncommon for horizontal permeabilities to be ten or more times greater than the vertical permeability. Knowledge of both horizontal and vertical permeabilities is important for at least two reasons. First, the horizontal permeability is a better indicator of the productivity of a reservoir than an average permeability determined by the methods discussed above. Secondly, the vertical permeability provides useful information to the production engineer of possible flow rates between different zones of a reservoir, information that is helpful in the setting of packers and of perforating casing in a well. It is to be noted that the terms "horizontal" and "vertical" as used in the present document generally refers to directions in which the permeability is a maximum and a minimum respectively. These are commonly, but not necessarily horizontal and vertical in an earth reference frame. Similarly, the term "horizontal" in connection with a borehole is one in which the borehole axis is parallel to a plane defined by the horizontal permeability.

U.S. Pat. No. 4,890,487 to Dussan et al. teaches a method for determining the horizontal and vertical permeabilities of a formation using measurements made with a single probe. The analysis is based on representing the fluid behavior during drawdown by an equation of the form:

$$P_f - P_i = \left( \frac{Q\mu}{2\pi r_p k_h} F\left(\frac{\pi}{2}, \sqrt{1 - k_V/k_H}\right) \right), \quad (1)$$

where
$P_f$ represents pressure of the undisturbed formation;
$P_i$ represents pressure at the end of draw-down period i;
$Q_i$ represents volumetric flow rate during draw-down period i;
$\mu$ represents dynamic viscosity of the formation fluid;
$r_p$ represents the probe aperture radius;

$k_H$ represents horizontal formation permeability;
$k_V$ represents vertical formation permeability; and
F denotes the complete elliptic integral of the first kind.

In Dussan, at least three sets of measurements are made, such as two drawdown measurements and one buildup measurement, and results from these are combined with a table lookup to give an estimate of vertical and horizontal permeability. The above equation was derived based on several assumptions: an infinite wellbore, constant drawdown rate and steady state flow. The steady state flow condition cannot be satisfied in a low permeability formation, or unless a long test time is used. A constant drawdown rate is not reachable in practice because the tool needs time for acceleration and deceleration. The storage effect also makes it difficult to reach a constant drawdown rate. The infinite wellbore assumption excludes the wellbore effect on the non-spherical flow pattern, making their method not inapplicable to high $k_H/k_V$ cases. The cases of $k_H/k_V<1$ were not presented in Dussan. The method works only in a homogeneous formation. However, their method does not have any procedure to check if the condition of homogeneous formation can be satisfied for a real probe test. The present invention addresses all of these limitations.

U.S. Pat. No. 5,265,015 to Auzerais et al. teaches determination of vertical and horizontal permeabilities using a special type of probe with an elongate cross-section, such as elliptic or rectangular. Measurements are made with two orientations of the probe, one with the axis of elongation parallel vertical, and one with the axis of elongation horizontal. The method requires a special tool configuration. To the best of our knowledge, there does not exist such a tool and it is probably difficult or expensive to build one. The present invention does not require a special tool, and such tool is available, for example, the one described in U.S. Pat. No. 6,478,096 to Jones et al.

U.S. Pat. No. 5,703,286 to Proett et al. teaches the determination of formation permeability by matching the pressure drawdown and buildup test data (possibly over many cycles). There is a suggestion that the method could be modified to deal with anisotropy and explicit equations are given for the use of multiple probes. However, there is no teaching on how to determine formation anisotropy from measurements made with a single probe. Based on the one equation given by Proett, it would be impossible to determine two parameters with measurements from a single probe. It would be desirable to have a method of determination of anisotropic permeabilities using a single probe. The present invention satisfies this need.

SUMMARY OF THE INVENTION

The present invention is a method of estimating, and apparatus for determining, permeability of an earth formation in at least one of two orthogonal directions. The formation contains a formation fluid. Fluid pressures are measured over a time interval in a probe conveyed in a substantially horizontal borehole in the earth formation. The probe is in hydraulic communication with the earth formation. For a time up to a defined time, fluid is withdrawn at a measured rate from the formation using the probe (drawdown). Pressure measurements are made during the drawdown. A first flow test is made with the probe against a side wall of the borehole. A second flow test is made with the probe against the upper or lower wall of the borehole. The horizontal and vertical permeabilities of the formation are estimated from permeability estimates obtained from the two flow tests.

In near horizontal boreholes, the formation tester may be conveyed on a drilling tubular or on coiled tubing. Alternatively, a downhole tool motor may be used and withdrawal from the borehole may be done using a wireline.

BRIEF DESCRIPTION OF THE DRAWINGS

The present invention is best understood with reference to the accompanying figures in which like numerals refer to like elements and in which.

DETAILED DESCRIPTION OF THE INVENTION

Figure 1:
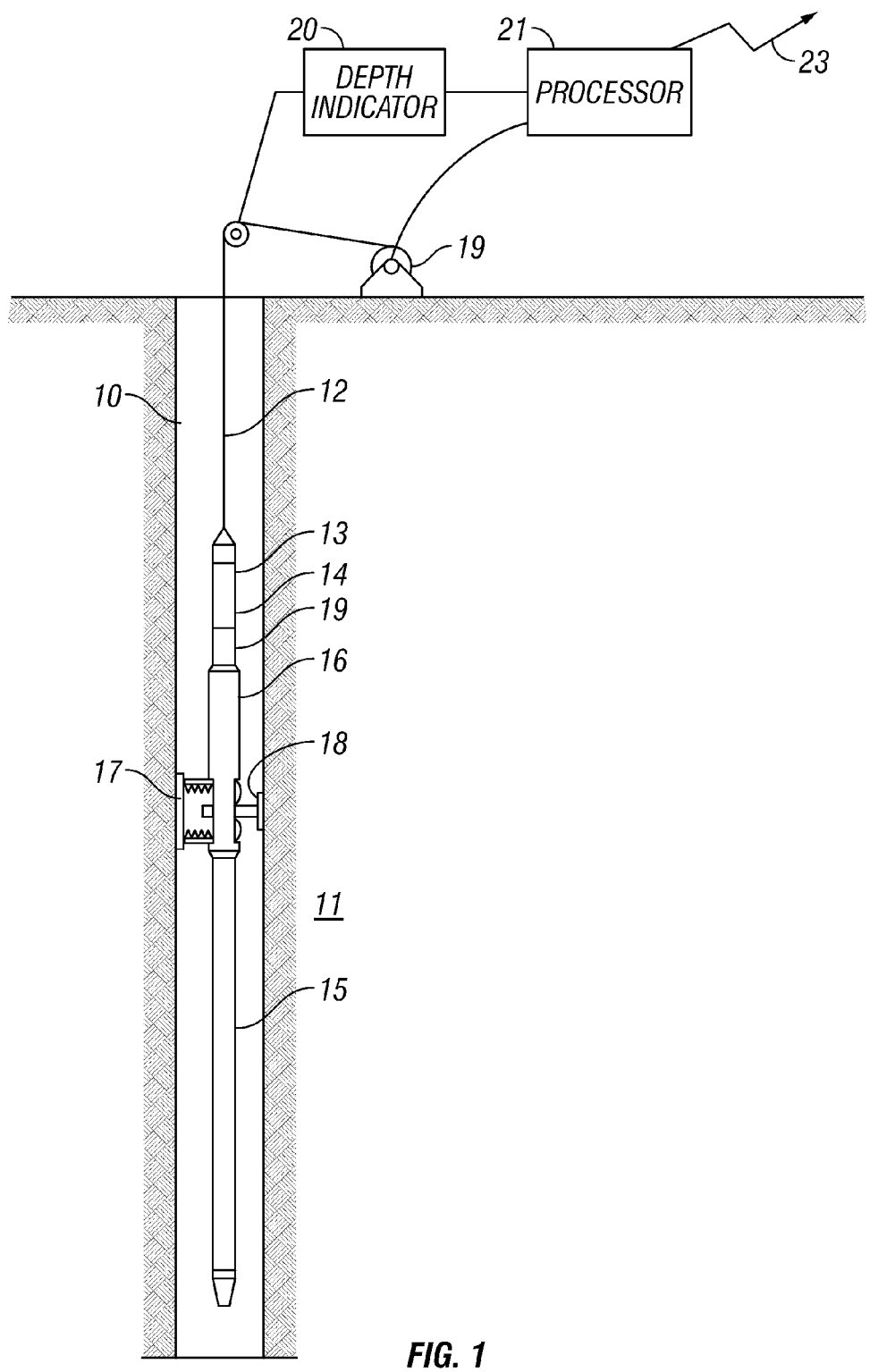
FIG. 1 (prior art) is an illustration of a wireline conveyed formation testing instrument positioned within a wellbore.

Referring now to FIG. 1, there is illustrated schematically a section of a borehole 10 penetrating a portion of the earth formations 11, shown in vertical section. Disposed within the borehole 10 by means of a cable or wireline 12 is a sampling and measuring instrument 13. The sampling and measuring instrument is comprised of a hydraulic power system 14, a fluid sample storage section 15 and a sampling mechanism section 16. Sampling mechanism section 16 includes selectively extensible well engaging pad member 17, a selectively extensible fluid admitting sampling probe member 18 and bi-directional pumping member 19. The pumping member 19 could also be located above the sampling probe member 18 if desired.

In operation, sampling and measuring instrument 13 is positioned within borehole 10 by winding or unwinding cable 12 from a hoist 19 around which cable 12 is spooled. Depth information from depth indicator 20 is coupled to processor 21. The processor analyzes the measurements made by the downhole tool. In one embodiment of the invention, some or all of the processing may be done with a downhole processor (not shown). A satellite link 23 may be provided to send the data to a remote location for processing.

For any formation testing tool, the flow measurement using a single probe is the cheapest and quickest way. The present invention provides two practical methods to estimate horizontal and vertical permeabilities from such probe test data. The first method is to combine the results of the two analyses, FRA and pressure buildup analysis. The second method is to combine the results of buildup analysis and pressure history matching. The probe test can be conducted using Baker Atlas's formation testing tool used under the service mark RCI$^{SM}$. Some details of the formation testing tool are described in U.S. Pat. No. 5,377,755 issued to Michaels et al., having the same assignee as the present invention and the contents of which are incorporated herein by reference.

Figure 2:
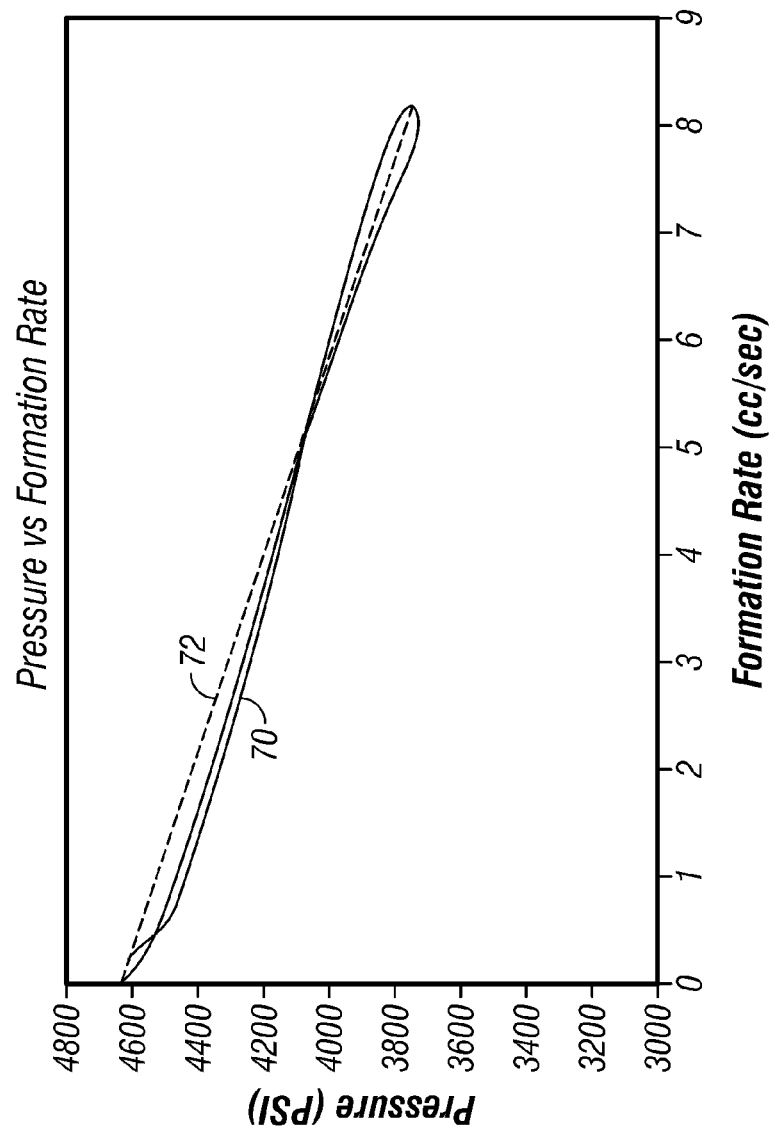
FIG. 2 (prior art) shows a graph of measured pressure with respect to fluid flow rate in the earth formation.

The method of the present invention uses data from a drawdown test and a pressure buildup test made with a single probe. The relationship between measured pressure and formation flow rate can be observed in the graph in FIG. 2. The pressure and flow rate measurements are shown as individual points connected by a curve 70. A linear regression analysis of the points on curve 70 can be used to generate a line 72 for which the slope can be calculated. The slope of line 72 is related to the fluid mobility.

As discussed in Sheng et al., if the non-spherical flow pattern is described using a geometric skin factor, $s_p$, the spherical drawdown solution may be written $$p_i - p(t) = \frac{q\mu}{4\pi k_s r_p}(1 + s_p) - \frac{q\mu}{4\pi k_s}\sqrt{\frac{\phi\mu c_t}{\pi k_s}}\frac{1}{\sqrt{t}}, \tag{2}$$

where
$c_t$ is the total formation compressibility, atm$^{-1}$;
$k_s$ is the spherical permeability, D;
$p(t)$ represents the measured pressure in the tool, atm;
$p_i$ is the initial formation pressure, atm;
q is the volumetric flow rate, cm$^3$/s;
$r_p$ is the true probe radius, cm;
$s_p$ is the geometric skin factor, dimensionless;
t is the time since the start of drawdown, s;
$\mu$ is the viscosity of fluid, cP; and
$\phi$ is the formation porosity, fraction.

The units of measurement are not relevant except as far as they pertain to specific numerical values derived later in this document.

The steady-state pressure drop for a single probe in an anisotropic formation was investigated by Dussan and Sharma (1992). On the basis that most of the pressure drop occurs in the vicinity of the probe and the probe is very small in relation to the wellbore, they treated the wellbore as being infinite in diameter ($r_w = \infty$). Their pressure drop is formulated by $$\Delta p(\eta, r_p, r_w = \infty) = \frac{q\mu}{2\pi\sqrt{k_H k_V}\max(r_p, r_p/\eta)}F(\frac{\pi}{2}, \sqrt{1-\eta^2}), \tag{3}$$

where $\eta = k_v/k_h$, and $F(\pi/2, e)$ is the complete elliptical integral of the first kind defined as $$F(\frac{\pi}{2}, e) = \int_0^1 \frac{dv}{\sqrt{(1-v^2)(1-e^2v^2)}}. \tag{4}$$

Note that F tends to $\pi/2$ as e defined as $\sqrt{1-\eta^2}$ tends to zero in an isotropic case.

Wilkinson and Hammond (1990) extended Dussan and Sharma's work to include a correction for the borehole radius by introducing a shape factor, $C_{eff}$. The shape factor is defined as $$C_{eff}(\eta, r_p, r_w) = \frac{\Delta p(\eta, r_p, r_w)}{\Delta p(\eta, r_p, r_w = \infty)}. \tag{5}$$

Then the pressure drop is $$\Delta p(\eta, r_p, r_w) = \frac{q\mu F(\frac{\pi}{2}, \sqrt{1-\eta^2})C_{eff}}{2\pi\sqrt{k_H k_V}\max(r_p, r_p/\eta)}, \text{where} \tag{6}$$

$$C_{eff} = 1 - \frac{\max(r_p, r_p/\eta)}{4r_w F(\frac{\pi}{2}, \sqrt{1-\eta^2})}\left[3.3417 + \ln\left(\frac{r_w \eta}{2r_p(1+\eta)}\right) - \frac{1}{1+\eta}\right]. \tag{7}$$

When the wellbore radius tends to infinity, $C_{eff}$ tends to 1, and eqn. 6 becomes identical to eqn. 3, as should be the case. In the FRA formulation, non-spherical flow geometry is considered by introducing a geometric factor, $G_0$. The pressure drop induced by a flow rate is $$\Delta p(\eta, r_p, r_w) = \frac{q\mu}{G_0 k_{FRA} r_p}, \tag{8}$$

where $k_{FRA}$ is the permeability estimated from the FRA technique.

By comparing eqns. 6 and 8, the values of $G_o$ can be derived from the values of F and $C_{eff}$ using the following equation $$G_0 = \frac{2\pi\sqrt{k_H k_V}\max(r_p, r_p/\eta)}{F(\frac{\pi}{2}, \sqrt{1-\eta^2})C_{eff} r_p k_{FRA}}. \tag{9}$$

Deriving the values of $G_0$ using the above equation depends on which permeability $k_{FRA}$ is (horizontal, vertical or spherical permeability). It also involves the calculation of the complete elliptical integral. Sometimes such calculation may not be performed easily, especially when $\eta^2$ is greater than one. It is also found that the values of $C_{eff}$ calculated using eqn. 7 are even larger than 1.0 in the cases of high $k_H/k_V$, which violates the fluid flow physics. This is attributable to violation of one of the assumptions used in the derivation of eqn 7 when $k_H/k_V$ is very large. In other words, eqn. 7 is not applicable in some cases. As a result, we may not be able to use eqn. 6 to calculate the pressure drop in some cases.

Wilkinson and Hammond (1990) corrected the values of $C_{eff}$ in the cases of high $k_H/k_V$. Based on the corrected, $C_{eff}$, they defined another parameter, $k_H/k_D$. Here $k_H$ is horizontal permeability, and $k_D$ is a drawdown permeability, defined as $$k_D = \frac{q\mu}{4r_p \Delta p}. \tag{10}$$

$k_D$ is computed as if the flow occurs in an isotropic formation and the borehole is infinite. In this case, the flow is a hemi-spherical flow, and the equivalent probe radius is $2r_p/\pi$. When eqn. 10 is used in an isotropic formation with an infinite wellbore, the estimated $k_D$ is the true formation permeability. When eqn. 10 is used in a real anisotropic formation with a real finite wellbore, the estimated $k_D$ may not represent the horizontal, vertical, or spherical permeability and is a function of $k_H/k_V$ and $r_p/r_w$. Because $k_D$ is a function of $k_H/k_V$ and $r_p/r_w$, we can use its values to derive the values for other geometric correction factors at different $k_H/k_V$ and $r_p/r_w$.

To estimate $G_o$, we compare eqn. 8 with eqn. 10, and get $$G_0 k_{FRA} = 4k_D = \frac{q\mu}{4r_p \Delta p}. \tag{11}$$

We note for a particular test that with the measured $q$ and $\Delta p$, and the fixed $\mu$, $r_p$, the product, $G_o k_{FRA}$, is fixed. $G_o$ and $k_{FRA}$ are related to each other by the relationship described by the above equation. In other words, depending on the type of permeability sought (e.g., horizontal, vertical, or spherical permeability), different values of $G_o$ are required. From eqn. 11, $$G_0 = \frac{4k_0}{k_{FRA}}. \tag{12}$$

If a spherical permeability from FRA is sought, then it is necessary to use the $G_{os}$ which corresponds to spherical permeability:

$$G_{os} = \frac{4}{k_s/k_D} = \frac{4}{(k_H^{2/3} k_V^{1/3}/k_D)} = \frac{4}{k_H/k_D}\left(\frac{k_H}{k_V}\right)^{1/3}. \tag{13}$$

Here spherical permeability has been assumed to be given by $k_s = \sqrt[3]{k_V k_H^2}$. From the published values of $k_H/k_D$ (Wilkinson and Hammond, 1990), the values of $G_{os}$ are readily obtained. The values as a function of $r_p/r_w$ and $k_H/k_V$ are tabulated in Table 1 and shown in FIG. 3.

TABLE 1

Numerical values of $G_{os}$ in FRA for various values of $r_p/r_w$ and anisotropy $k_H/k_V$

| | $r_p/r_w =$ | | | | |
|---|---|---|---|---|---|
| $k_H/k_V$ | 0.025 | 0.05 | 0.1 | 0.2 | 0.3 |
| 0.01 | 3.75 | 3.75 | 3.75 | 3.92 | 3.92 |
| 0.1 | 3.64 | 3.64 | 3.71 | 3.87 | 3.95 |
| 1 | 4.08 | 4.17 | 4.26 | 4.44 | 4.65 |
| 10 | 5.42 | 5.56 | 5.78 | 6.11 | 6.38 |
| 100 | 8.33 | 8.60 | 9.06 | 9.72 | 10.26 |
| 1000 | 14.18 | 14.87 | 15.81 | 17.09 | 18.02 |
| 10000 | 25.96 | 27.45 | 29.31 | 31.57 | 33.15 |
| 100000 | 49.64 | 52.60 | 55.92 | 59.89 | 62.51 |
| 1000000 | 97.09 | 102.30 | 108.40 | 115.27 | 119.76 |

Figure 3:
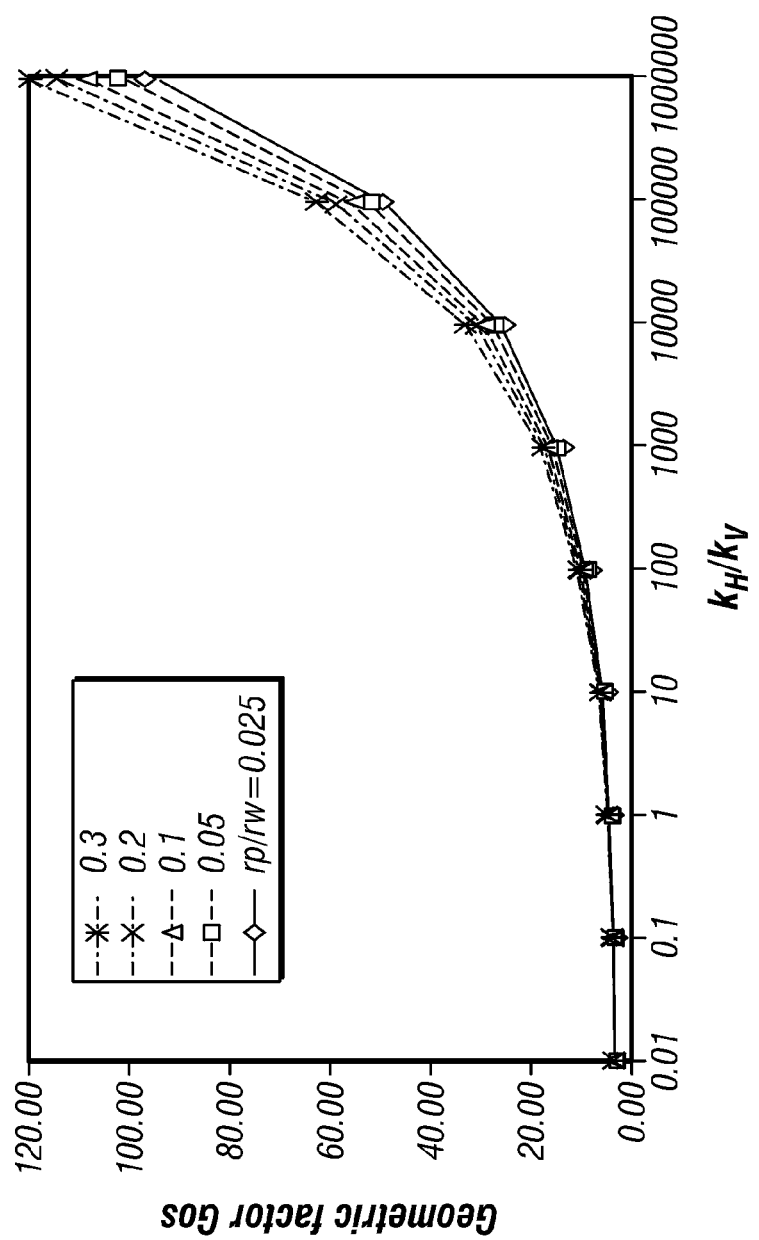
FIG. 3 shows numerical values of the $G_{os}$ in FRA for various values of $r_p/r_w$ and anisotropy $k_H/k_V$.

From Table 1 and FIG. 3, we see that the geometric factor is a strong function of anisotropy and a weak function of $r_p/r_w$. Also, the values of $G_{os}$ for $k_H/k_V$ from 1 to 100 calculated from eqn. 13 are in close agreement with those calculated from eqn. 9 in which $C_{\mathit{eff}}$ is calculated using eqn. 7.

The concept of geometric skin was proposed to represent the above defined geometric factor (Strauss, 2002). Defining a geometric skin factor $s_p$ to account for the deviation from the true spherical flow gives $$\Delta p = \frac{q\mu(1+s_p)}{4\pi k_s r_p}. \tag{14}$$

Comparing eqns. 10 and eqn. 14, $s_p$ can be estimated from $$s_p = \frac{\pi(k_H/k_V)}{(k_H/k_V)^{1/3}} - 1. \tag{15}$$

Figure 4:
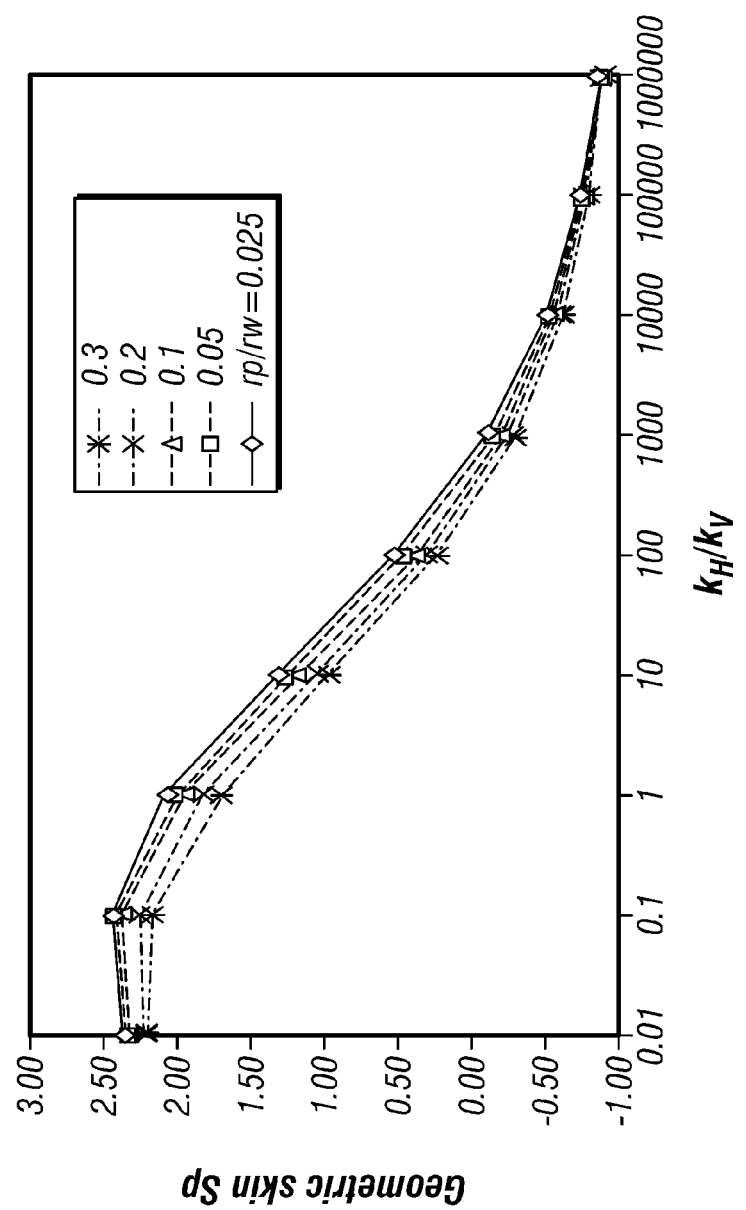
FIG. 4 shows numerical values of the $s_p$ for various values of $r_p/r_w$ and anisotropy $k_H/k_V$.

Again from the published values of $k_H/k_D$ (Wilkinson and Hammond, 1990), the values of $s_p$ are readily obtained. The values as a function of $r_p/r_w$ and $k_H/k_D$ are tabulated in Table 2 and shown in FIG. 4.

TABLE 2

Numerical values of $s_p$ for various values of $r_p/r_w$ and anisotropy $k_H/k_V$

| | $r_p/r_w =$ | | | | |
|---|---|---|---|---|---|
| $k_H/k_V$ | 0.025 | 0.05 | 0.1 | 0.2 | 0.3 |
| 0.01 | 2.35 | 2.35 | 2.35 | 2.21 | 2.21 |
| 0.1 | 2.45 | 2.45 | 2.38 | 2.25 | 2.18 |
| 1 | 2.08 | 2.02 | 1.95 | 1.83 | 1.70 |
| 10 | 1.32 | 1.26 | 1.17 | 1.06 | 0.97 |
| 100 | 0.51 | 0.46 | 0.39 | 0.29 | 0.23 |
| 1000 | −0.11 | −0.15 | −0.21 | −0.26 | −0.30 |
| 10000 | −0.52 | −0.54 | −0.57 | −0.60 | −0.62 |
| 100000 | −0.75 | −0.76 | −0.78 | −0.79 | −0.80 |
| 1000000 | −0.87 | −0.88 | −0.88 | −0.89 | −0.90 |

Again, there is little dependence on the probe packer size as measured by the dimensionless probe size, $r_p r_w$.

If we can define an equivalent probe radius, $r_{ep}$, to account for the deviation from true spherical flow, we can write $$\Delta p = \frac{q\mu}{4\pi k_s r_{sp}}. \tag{16}$$

Comparing eqns. 10 and 16, $r_{ep}$ can be estimated from $$r_{ep} = \frac{r_p (k_H/k_V)^{1/3}}{\pi(k_H/k_D)}. \tag{17}$$

Figure 5:
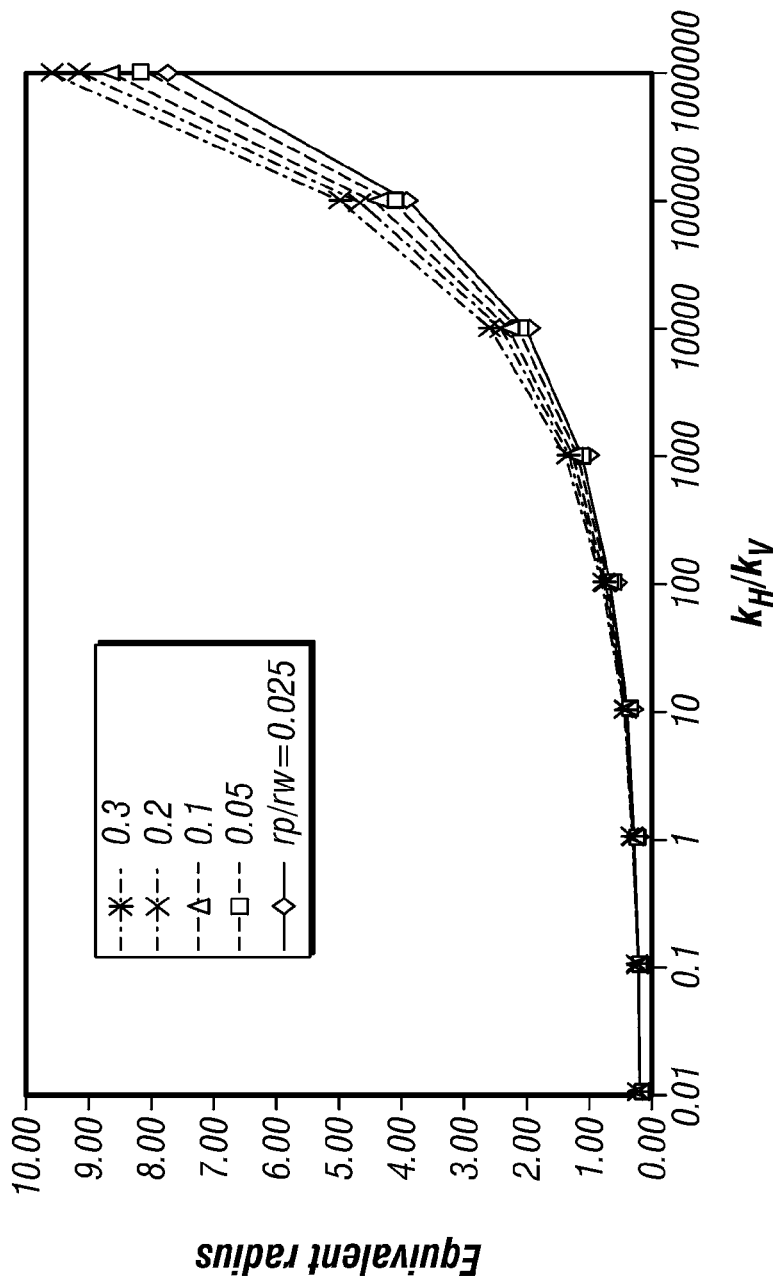
FIG. 5 shows numerical values of the $r_{ep}$ for various values of $r_p/r_w$ and anisotropy $k_H/k_V$.

Using the published values of $k_H/k_D$ (Wilkinson and Hammond, 1990), the values of $r_{ep}$ are readily obtained. The values as a function of $r_p/r_w$ and $k_H/k_V$ are tabulated in Table 3 and shown in FIG. 5.

TABLE 3

Numerical values of the $r_{ep}/r_p$ for various values of $r_p/r_w$ and anisotropy $k_H/k_v$.

| $k_H/k_V$ | $r_p/r_w =$ 0.025 | 0.05 | 0.1 | 0.2 | 0.3 |
|---|---|---|---|---|---|
| 0.01 | 0.30 | 0.30 | 0.30 | 0.31 | 0.31 |
| 0.1 | 0.29 | 0.29 | 0.30 | 0.31 | 0.31 |
| 1 | 0.32 | 0.33 | 0.34 | 0.35 | 0.37 |
| 10 | 0.43 | 0.44 | 0.46 | 0.49 | 0.51 |
| 100 | 0.66 | 0.68 | 0.72 | 0.77 | 0.82 |
| 1000 | 1.13 | 1.18 | 1.26 | 1.36 | 1.43 |
| 10000 | 2.07 | 2.18 | 2.33 | 2.51 | 2.64 |
| 100000 | 3.95 | 4.19 | 4.45 | 4.77 | 4.97 |
| 1000000 | 7.73 | 8.14 | 8.63 | 9.17 | 9.53 |

The formulations and values of the above correction factors are based on the related spherical flow eqns. 8, 14, or 16. For eqn. 6, $k_{FRA}$ is assumed to be the spherical permeability. Comparing their defining eqns. 11, 13, and 15, it can be seen that these three correction factors have the following relationship:

$$s_p + 1 = \frac{4\pi}{G_{os}} = \frac{1}{r_{ep}/r_p}; \text{ or,} \quad (18)$$

$$s_p + 1 = \frac{4\pi}{G_{os}}, \quad (19)$$

$$\frac{1}{r_{ep}/r_p} = \frac{4\pi}{G_{os}}. \quad (19a)$$

Substituting from eqn. 19 into eqn. 2, gives:

$$p_i - p(t) = \frac{q\mu}{G_{os}k_s r_p} - \frac{q\mu}{4\pi k_s}\sqrt{\frac{\phi\mu c_t}{\pi k_s}}\frac{1}{\sqrt{t}}. \quad (20)$$

Eqns. 2 and 20 are valid for both isotropic and anisotropic formations. Using the principle of superposition, the buildup solution is $$p(t) = p_i - \frac{q\mu}{4\pi k_s}\sqrt{\frac{\phi\mu c_t}{\pi k_s}}\left(\frac{1}{\sqrt{\Delta t}} - \frac{1}{\sqrt{t}}\right), \quad (21)$$

where $\Delta t$ is the shut-in time, s. Here, q is the flow rate for the previous drawdown measurement. According to eqn. 20, the buildup mobility is estimated from $$\left(\frac{k_s}{\mu}\right)_{BU} = \frac{1}{\pi}\left(\frac{q}{4m_s}\right)^{2/3}(\phi c_t)^{1/3}, \quad (22)$$

where $m_s$ is the slope of the linear plot of p(t) vs. the time function $(\Delta t^{-1/2} - t^{-1/2})$.

For the purposes of the present invention, the permeability measured using the buildup measurements is referred to as a first permeability.

Turning now to the FRA method as described in Kasap, $$p(t) = p_i - \frac{q_f \mu}{k_s G_{os} r_p}, \quad (23)$$

where $q_f$, the formation flow rate at the sand face near the probe, is $$q_f = c_{sys}V_{sys}\frac{dp(t)}{dt} + q_{dd}, \quad (24)$$

corrected for the storage effect. In the above equation, $c_{sys}$ is the compressibility of the fluid in the tool, atm$^{-1}$; $q_{dd}$ is the piston withdrawal rate, cm$^3$/s; $V_{sys}$ is the system (flow line) volume, cm$^3$.

According to FRA, the data in both drawdown and buildup periods are combined to estimate the mobility from $$\left(\frac{k_s}{\mu}\right)_{FRA} = \frac{1}{G_{os}r_p m_{FRA}}, \quad (25)$$

where $m_{FRA}$ is the slope of the linear plot of p(t) vs. $q_f$. By plotting the drawdown data and the buildup data in the FRA plot (FIG. 2), if both data are seen to fall on the same straight line with a slope, $m_{FRA}$, the estimated permeability from the drawdown and the buildup is the same. That means within the radius of investigation for the drawdown and buildup, the formation is homogeneous. This is the condition for the presented methods to work.

Eqn. 25 shows that the estimated mobility from FRA is affected by the local flow geometry indicated by $G_{os}$. Thus, a correct value of $G_{os}$ must be provided. However, $G_{os}$ strongly depends on the ratio of vertical-to-horizontal permeability that is generally unknown before the test is performed. In this case, the value of $G_{os}$ in an isotropic formation is used. As a result, the FRA estimated permeability may not represent the true spherical permeability. In contrast, the spherical permeability can be obtained from a buildup analysis without prior knowledge of formation anisotropy, and the estimate of mobility from the buildup analysis is not affected by the local flow geometry according to eqn. 22. In other words, the correct estimate of spherical permeability can be obtained from buildup analysis without knowing formation anisotropy and local flow geometry. The difference in the estimated spherical permeability from buildup analysis and FRA, discussed in the above, can be used to estimate the horizontal and vertical permeabilities. For the purposes of the present invention, the permeability determined by FRA processing is referred to as a second permeability.

The difference in the estimated spherical permeability from buildup analysis (the first permeability) and FRA permeability (the second permeability), discussed in the above, can be used to estimate the horizontal and vertical permeabilities. A simulated probe-pressure test data as an example is used to illustrate the procedures. First, the probe-pressure test simulation is described.

The simulation model used is given in Table 4.

TABLE 4

| Input parameters used in simulation | |
| --- | --- |
| Porosity, fraction | 0.2 |
| Spherical permeability, mD | 10 |
| $k_H/k_V$ | 10 |
| Viscosity, cP | 1 |
| Formation pressure, psi | 4000 |
| Fluid compressibility, 1/psi | 2.50E−06 |
| Wellbore radius, cm. | 6.35 |
| Probe radius, cm | 0.635 |
| Flow line volume, ml | 371 |
| Drawdown rate, ml/s | 4 |
| Duration of drawdown, s | 10 |

The symmetry in the problem is used to reduce the model to one quarter of the probe and the formation. Further, the effect of gravity is neglected. The model is a radial model. The $k_H/k_V$ is equal to 10 with the spherical permeability of 10 mD. The $r_p/r_w$ is equal to 0.1. The drawdown rate for the quarter model is 1 ml/s.

Figure 6:
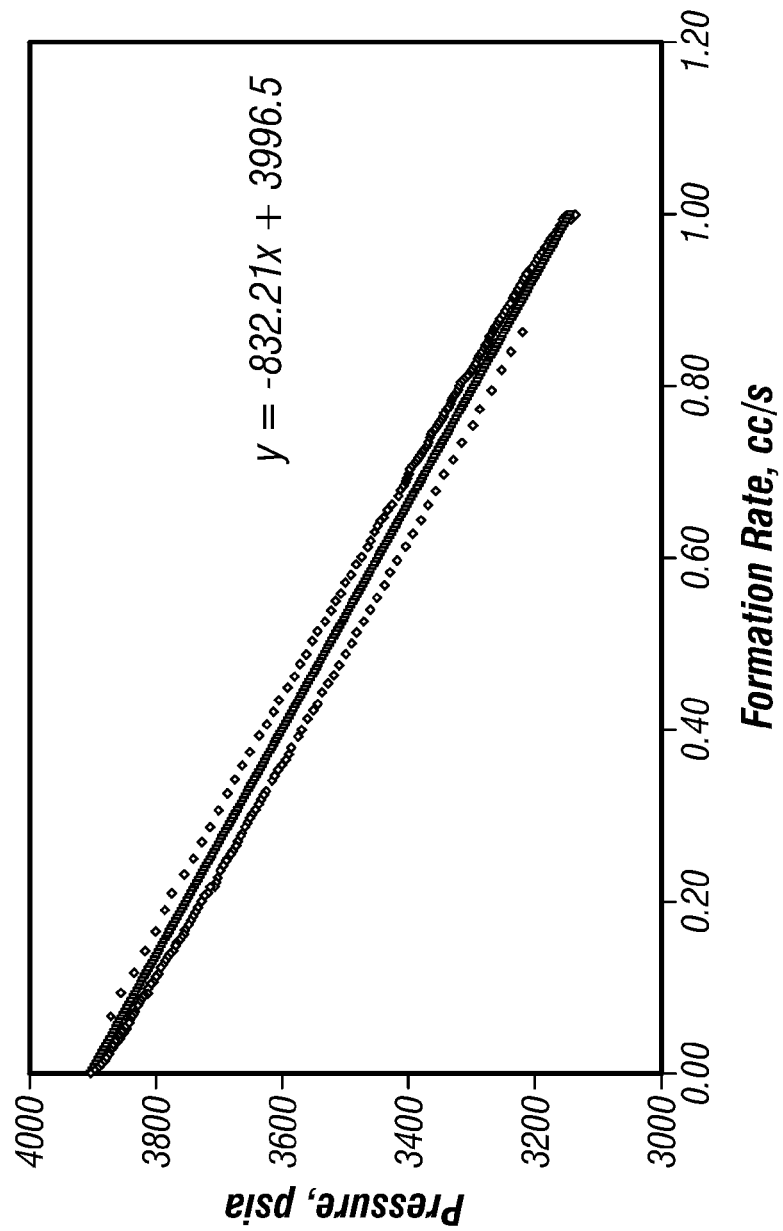
FIG. 6 is an FRA plot for the simulated probe test with $k_H/k_V=10$.

Next, results of analyzing the simulation data using the FRA technique are discussed. FIG. 6 shows the expected linear relation between the pressure and the formation flow rate. If the data were real probe-pressure test data and $k_H/k_V$ were unknown, one could logically assume the formation were isotropic. According to Table 1, the geometric factor, $G_{os}$, would be 4.26 for $r_p/r_w$ equal to 0.1. Based on eqn. 25 and using this value of $G_{os}$, one would estimate a spherical permeability of 13 mD.

Figure 7:
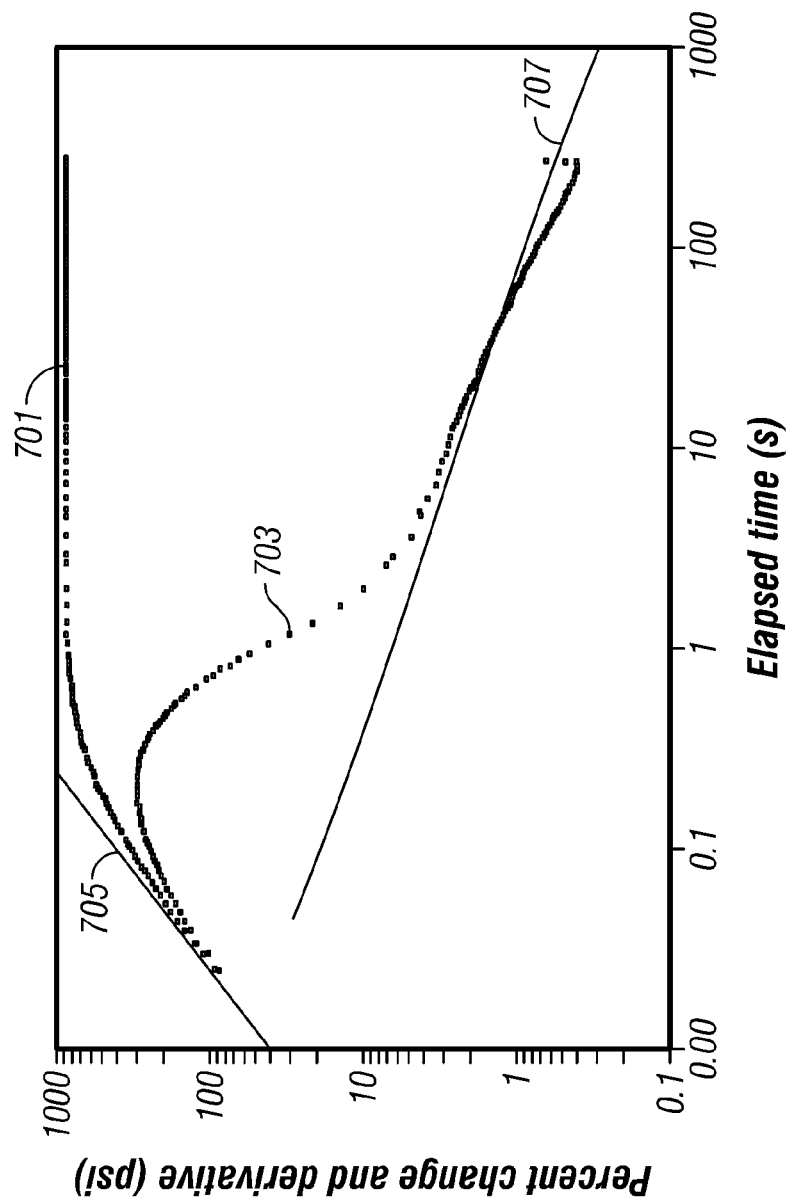
FIG. 7 is a plot of pressure changes and pressure derivatives for buildup data.

The simulated pressure test data could also be analyzed using buildup (BU) analysis using any pressure transient analysis software with spherical flow solutions. For this example, the commercially available software Interpret 2003 of Paradigm Geophysical Co was used. FIG. 7 shows the buildup analysis plot to estimate the spherical permeability for this case. The abscissa is time and ordinate is the pressure change 701 or the pressure derivative 703. The plot is on a log-log scale. Also shown on the plot are lines with a slop of +1 (705) and a slope of −½ (707). The spherical flow regime is identified by a negative half slope in the log-log derivative plot. From this buildup analysis, the spherical permeability is estimated to be 9.62 mD, close to the input spherical permeability. It should be noted that the use of the Interpret2003 software is for exemplary purposes only and other software packages that perform similar functions (as described below) could be used.

For the same pressure data, different estimates of permeability are obtained from buildup analysis and from FRA. One is 13 mD from FRA, the other is 9.62 mD from the BU analysis. The latter is close to the actual permeability used in the simulation model. The former is different from the actual permeability because we used an incorrect $G_{os}$. To make FRA estimated permeability closer to the actual one used in the simulation, a value of $G_{os}$ appropriate for the permeability anisotropy ratio in the simulation should be used. Assuming the BU estimated spherical permeability is correct, the correct $G_{os}$ can be estimated as follows.

$$(k_s G_{os})_{FRA} = \frac{\mu}{r_p m_{FRA}}, \quad (26)$$

The above shows that for a particular test, since the linear relationship between the measured q and Δp results in a constant slope, $m_{FRA}$, for the fixed μ and $r_p$, the product, $(G_{os}k_s)_{FRA}$, is fixed. In other words, for a particular test, if an isotropic formation is assumed for FRA, then $(G_{os}k_s)$ in the isotropic formation, denoted by $(G_{os}k_s)_{iso}$, should equal the permeability-geometric factor product of the anisotropic formation, $(G_{os}k_s)_{ani}$. This product consists of the correct $G_{os}$ and the correct $k_s$ in the anisotropic formation. Because the BU estimated permeability is assumed to be the true spherical permeability, then the correct $G_{os}$ in the anisotropic formation, $(G_o)_{ani}$, can be estimated from $$(G_{os})_{ani} = \frac{(G_{os}k_s)_{iso}}{(k_s)_{BU}}. \quad (27)$$

In the term $(G_{os}k_s)_{iso}$ of the above equation, $G_{os}$ is the geometric factor for an isotropic formation ($G_{os}$=4.26 from Table 1), and $k_s$ is the FRA permeability estimated initially assuming the formation is isotropic. For this example, $k_s$ is 13 mD. In the denominator, $(k_s)_{BU}$ is the spherical permeability estimated from the buildup analysis which is 9.62 mD in this example. Therefore, the correct $G_{os}$ in this example is $$(G_{os})_{ani} = \frac{(G_{os}k_s)_{iso}}{(k_s)_{BU}} = \frac{(4.26)(13)}{9.62} = 5.76. \quad (28)$$

The estimated $G_{os}$ of 5.76 is very close to the $G_{os}$ in FIG. 1 when $k_H/k_V$ is equal to 10 and $r_p/r_w$ is equal to 0.1. Therefore, by combining the results of FRA and buildup analysis, it is possible to determine $k_H/k_V$. Having $k_H/k_V$ determined, the horizontal permeability and vertical permeability are readily obtained:

$$k_H = (k_s)_{BU}/(k_H/k_V)^{(1/3)}, \quad (29),$$

$$k_V = k_H/(k_H/k_V). \quad (30).$$

For this example, the calculated horizontal permeability and vertical permeability are 20.7 mD and 2.07 mD, respectively. These values are very close to their respective simulation model input values of 21.54 mD and 2.15 mD. Thus the method to combine FRA and buildup analysis is demonstrated.

Figure 8:
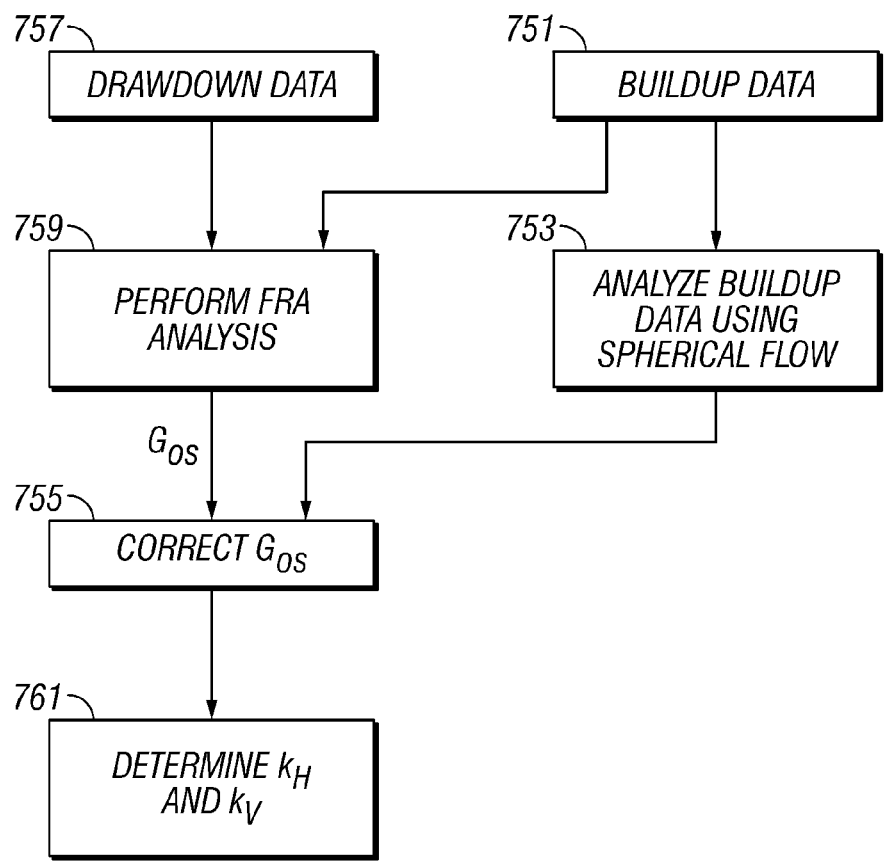
FIG. 8 is a flow chart illustrating one embodiment of the present invention for determining horizontal and vertical permeabilities from buildup and FRA analysis.

FIG. 8 is a flow chart illustrating the first embodiment of the invention. Pressure buildup data 751 are analyzed to get a first estimate of spherical permeability. Separately, the pressure buildup data 751 and the drawdown data 757 are analyzed to get a second estimate of spherical permeability 759. Using the two different permeabilities, the geometric factor $G_{os}$ for the probe is corrected 755 and using the corrected $G_{os}$, the horizontal and vertical permeabilities are determined as discussed above.

Figure 9:
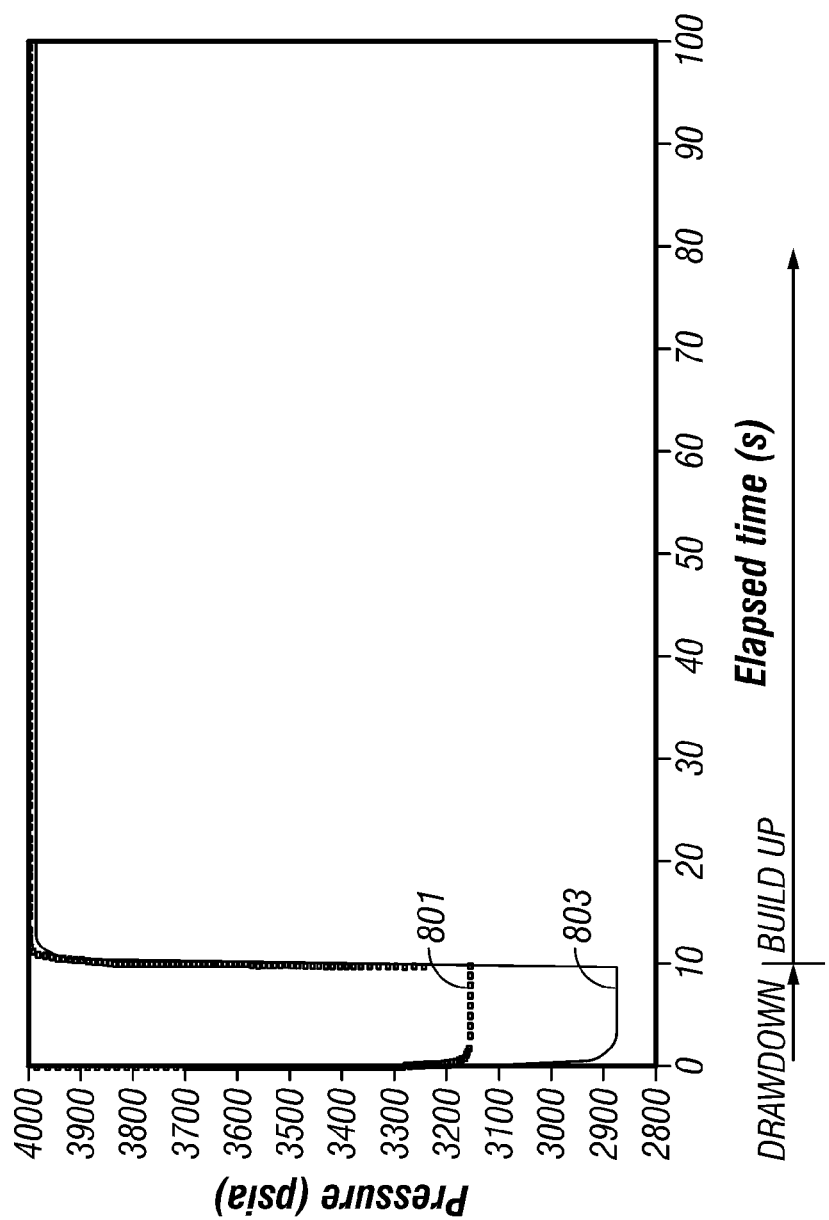
FIG. 9 is a comparison of simulated pressure data with an analytical spherical solution derived using the buildup permeability and an isotropic skin factor.

A second embodiment of the present invention uses the spherical permeability obtained from the pressure buildup test (the first permeability) as a starting point for matching the entire pressure history, including the drawdown data. In Interpret2003 the geometric skin factor, $s_p$, is used to describe the non-spherical flow near the probe. Even though the local geometry near the probe does not affect the permeability estimate, it does affect the pressure data as given by eqn. 2. In the above example, using the BU estimated permeability of 9.62 mD and an isotropic geometric skin factor of 1.95 shown in Table 1, the pressure data from Interpret2003 cannot be matched with the simulated pressure data because we used the wrong isotropic geometric skin factor. This is shown in FIG. 9 where the abscissa is time and the ordinate is pressure. The buildup portion is used to derive the permeability and this derived permeability is used to model the pressure data. More obviously, the modeled drawdown data 803 does not match the actual drawdown data 801. To match the simulated pressure data, it is necessary to use the BU estimated spherical permeability, and also to change the value of $s_p$ until the pressure data from Interpret2003 matches the numerical simulation data. It is found that using a value of $s_p$ equal to 1.2, a good match is obtained (not shown). From Table 2 it can be seen that $s_p$ equal to 1.2 (close the $s_p$ of 1.17 in Table 1) corresponds to $k_H/k_V$ equal to 10 and $r_p/r_w$ equal to 0.1. As above, $k_H/k_V$ has been estimated to be equal to 10. Once $k_H/k_V$ is obtained, eqns 28 and 29 can be used to estimate the horizontal and vertical permeabilities. Thus, the second method also uses a permeability from BU analysis (the first method) in combination with matching the entire pressure data (processing of data over the entire time interval including drawdown and buildup) to estimate horizontal and vertical permeabilities.

Conceptually, the second method is based on deriving a spherical permeability based on a buildup analysis, and then using this determined spherical permeability to match the pressure history data by adjusting the geometric skin factor. Knowledge of the spherical permeability and the geometric skin factor makes it possible to determine the horizontal and vertical permeabilities.

The two embodiments of the present invention discussed above are used to estimate horizontal and vertical permeabilities based on the assumption of a homogeneous and anisotropic formation. Such an assumption is reasonable in a practical probe test, because the formation on the small scale near the probe probably can be considered virtually homogeneous. Therefore, the invention provides a way to estimate the horizontal and vertical permeabilities from a single probe test without additional information. This is in contrast to prior art methods that require simultaneous measurements with multiple probes, or measurements with a specially designed probe in two orientations.

Figure 10A:
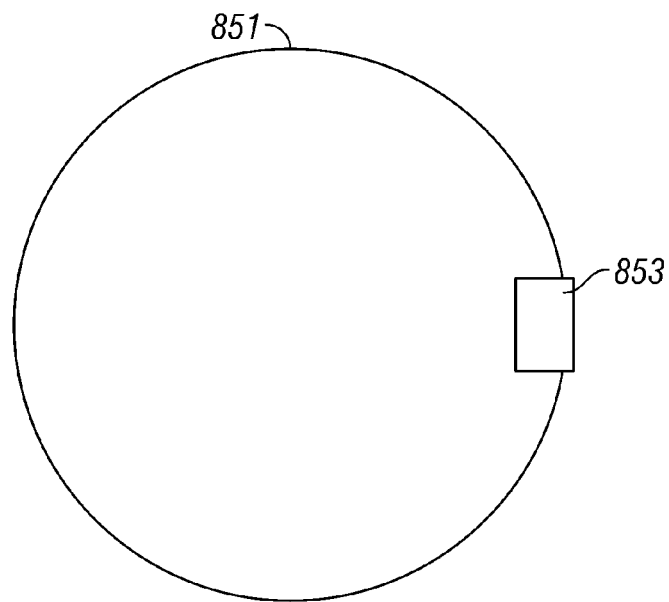
FIGS. 10a, 10b shows use of a probe for two measurements in a near horizontal borehole.
Figure 10B:
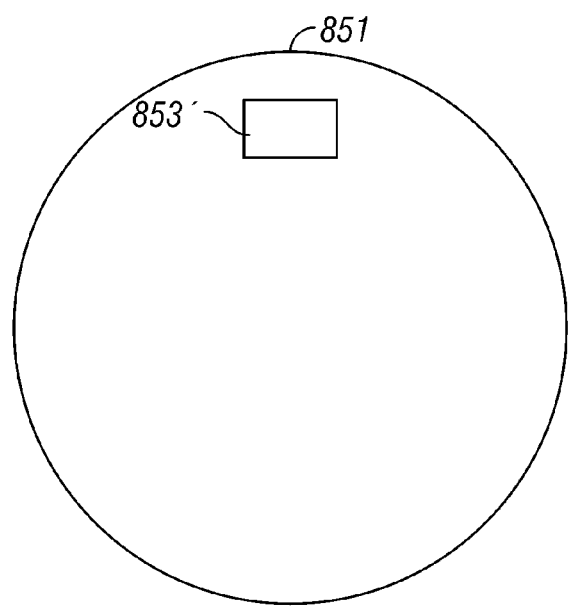

In another embodiment of the invention, two tests are made in a near horizontal borehole. In one test, the probe is set and sealed horizontally against a side wall of the borehole. This is schematically illustrated in FIG. 10a wherein the borehole 851 is shown in cross-section and a probe 853 is in contact with the side wall of the borehole. In a second test, schematically illustrated in FIG. 10b, the probe 853 is shown against the upper wall of the borehole. It is to be noted that the method is equally applicable if, in the second test, the probe is against the bottom wall of the borehole.

The solution for the first test is the same as that in a vertical well, and has been discussed above. The solution for the second test is derived next. The objective is to determine the relationship between the pressure at the probe and the fluid withdrawal rate from the anisotropic formation. As before, a cylindrical coordinate system is used in which the wellbore wall near the probe can be approximated by the z=0 plane, with the formation located in the half-space $z \geq 0$. The initial formation pressure is $p_i$. The z axis for the test of FIG. 10b coincides with the vertical direction. The perimeter of the probe opening through which fluid flows is given by $r^2 = r_p^2$ at z=0. The flowing pressure at the probe opening is $p_p$. There is no flow across the rest of the plane at z=0. The mathematical description of such probe test is a mixed boundary problem. Its formulation is given as follows.

$$k_H\left(\frac{\partial^2 p}{\partial r^2} + \frac{1}{r}\frac{\partial p}{\partial r}\right) + k_V \frac{\partial^2 p}{\partial z^2} = 0, \quad (31)$$

$$p = p_p \text{ at } r \leq r_p \text{ and } z = 0, \quad (32)$$

$$\frac{\partial p}{\partial z} = 0 \text{ at } r > r_p \text{ and } z = 0, \quad (33)$$

$$p \to p_i \text{ as } r^2 + z^2 \to \infty \text{ and } z \geq 0, \quad (34)$$

Of interest is the relationship between pressure drop, $p_i - p_p$, and flow rate, q. This is done by evaluating the integral:

$$q = \frac{2\pi k_V}{\mu} \int_{A_p} \left.\frac{\partial p}{\partial z}\right|_{z=0} r dr. \quad (35)$$

In the above equations,
$A_p$ represents area of probe opening, cm$^2$
$k_H$ represents horizontal permeability, D
$k_V$ represents vertical permeability, D
p represents pressure, atm
$p_i$ represents initial formation pressure, atm
$p_p$ represents pressure at the probe, atm
q represents volumetric flow rate, cm$^3$/s
r represents radial coordinate of cylindrical grid system, cm
$r_p$ represents true probe radius, cm
z represents z axis in the coordinate system, cm
μ represents viscosity of fluid, cP The units of measurement are not relevant except as far as they are consistently follow one unit system. Here Darcy unit system is used.

Using the following notation:

$$r' = r, \quad (36)$$

$$z' = \sqrt{\frac{k_H}{k_V}} z, \quad (37)$$

the above mathematical formulation (Eqns 31 to 35) is converted in the following formulation:

$$\left(\frac{\partial^2 p}{\partial r'^2} + \frac{1}{r'}\frac{\partial p}{\partial r'}\right) + \frac{\partial^2 p}{\partial z'^2} = 0, \quad (31')$$

$$p = p_p \text{ at } r' \leq r_p \text{ and } z' = 0, \quad (32')$$

$$\frac{\partial p}{\partial z'} = 0 \text{ at } r' > r_p \text{ and } z' = 0, \quad (33')$$

$$p \to p_i \text{ as } r'^2 + \frac{z'^2}{k_H/k_V} \to \infty \text{ and } z' \geq 0, \quad (34')$$

$$q = \frac{2\pi\sqrt{k_H k_V}}{\mu} \int_{A_p} \left.\frac{\partial p}{\partial z'}\right|_{z'=0} r' dr'. \quad (35')$$

The solution for the above problem was solved by Carslaw, H. S. and Jaeger, J. C., *Conduction of Heat in*

*Solids*, Oxford University Press (1959). According to their solution, the relationship between pressure drop and flow rate for the above problem is $$q = \frac{4\sqrt{k_H k_V}\, r_p (p_i - p_p)}{\mu}. \qquad (38)$$

Note that from the above equation, it is possible to obtain a permeability $(k_H k_V)^{1/2}$, a geometric average permeability of horizontal permeability and vertical permeability.

For the first test with the probe set horizontally against the side wall (FIG. 10a) in a horizontal well, the relationship between the pressure drop and flow rate is the same as that in a vertical well. Using the geometric factor and horizontal permeability, the relationship derived above is $$p_i - p_p = \frac{q\mu}{G_{oH} k_H r_p},$$

where $G_{oH}$ is the geometric factor when the pressure drop vs. flow rate relationship is formulated using horizontal permeability, $k_H$. Its values at different $k_H/k_V$ and $r_p/r_w$ are reported in the same reference and reprinted here in Table 5. Here $r_w$ is the radius of wellbore. Note that the values in Table 5 are for $G_{OH}$, related to a horizontal permeability whereas the values in Table 1 are for $G_{OS}$, related to a spherical permeability.

TABLE 5

Numerical values of $G_{oH}$ (for $k_H$) for various values of $r_p/r_w$ and anisotropy $k_H/k_V$

| | $r_p/r_w$ = | | | | |
|---|---|---|---|---|---|
| $k_H/k_V$ | 0.025 | 0.05 | 0.1 | 0.2 | 0.3 |
| 0.01 | 17.39 | 17.39 | 17.39 | 18.18 | 18.18 |
| 0.1 | 7.84 | 7.84 | 8.00 | 8.33 | 8.51 |
| 1 | 4.08 | 4.17 | 4.26 | 4.44 | 4.65 |
| 10 | 2.52 | 2.58 | 2.68 | 2.84 | 2.96 |
| 100 | 1.79 | 1.85 | 1.95 | 2.09 | 2.21 |
| 1000 | 1.42 | 1.49 | 1.58 | 1.71 | 1.80 |
| 10000 | 1.20 | 1.27 | 1.36 | 1.47 | 1.54 |
| 100000 | 1.07 | 1.13 | 1.20 | 1.29 | 1.35 |
| 1000000 | 0.97 | 1.02 | 1.08 | 1.15 | 1.20 |

From Eqn. 39, the horizontal permeability can be obtained. But this permeability is closely related to the geometric factor which is a strong function of $k_H/k_V$. Before analyzing the test data, $k_H/k_V$ is unknown. However, for a particular test with the measured q and $p_p$, and the fixed $\mu$, $r_p$, the product $G_{oH} k_H$ is a determined quantity. For the second test in a horizontal well when the probe is set vertically against the top wall of the borehole (FIG. 10b), the relationship between the pressure drop and flow rate is described by Eqn. 38 and a mean permeability, $(k_H k_V)^{1/2}$ can be obtained. In other words, when the two tests are conducted at the same measured depth, the following two quantities are obtained:

$$K_S \equiv G_{oH} k_H = \frac{q_S \mu}{r_p(p_i - p_{p,S})}, \qquad (40)$$

$$K_T \equiv \sqrt{k_H k_V} = \frac{q_T \mu}{4 r_p (p_i - p_{p,T})}, \qquad (41)$$

where the subscripts S and T means the probe is set horizontally against the side wall and vertically against the top wall, respectively. Both $K_S$ and $K_T$ are functions of permeability anisotropy, $k_H/k_V$. Now we define another quantity K using these two quantities:

$$K \equiv \frac{K_S}{K_T} = G_{oH} \sqrt{\frac{k_H}{k_V}}. \qquad (12)$$

Figure 11:
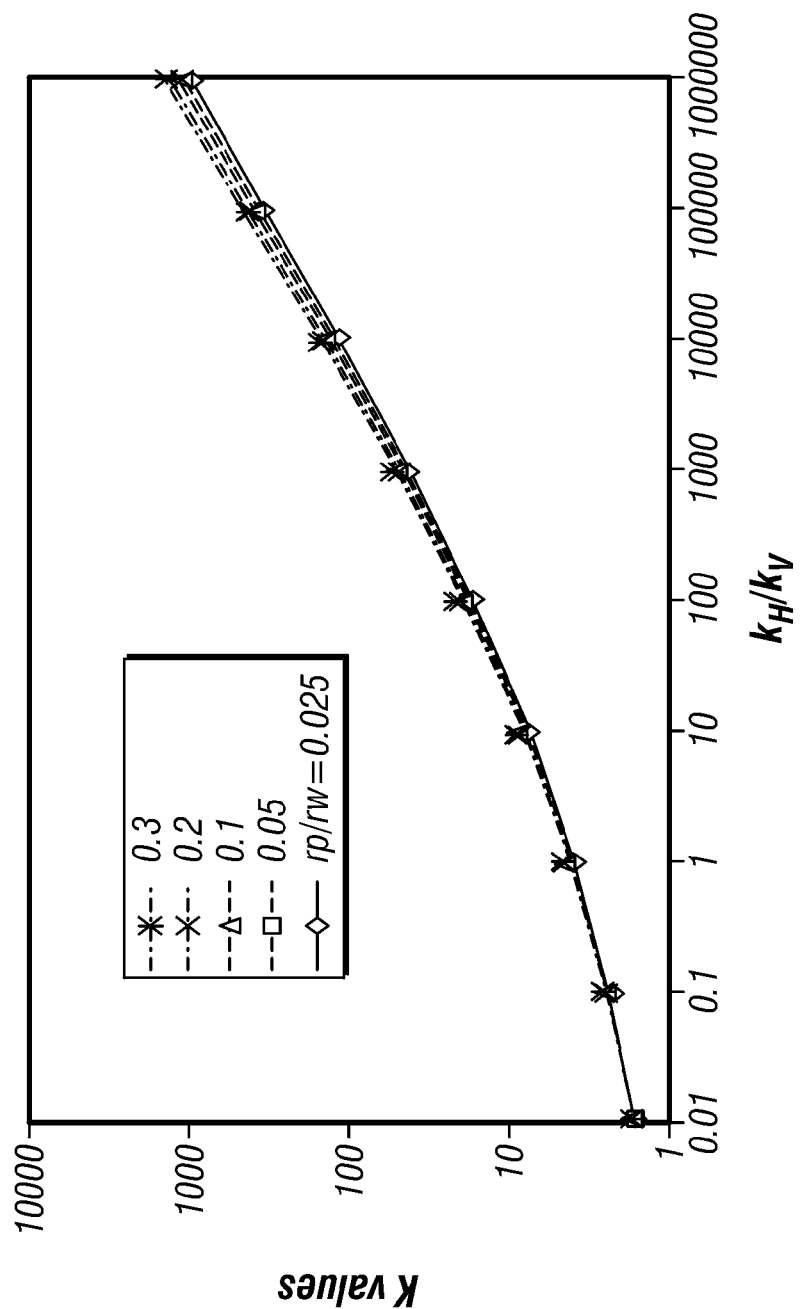
FIG. 11 shows K values for various values of $r_p/r_w$ and anisotropy $k_H/k_V$.

Because $G_{oH}$ is a function of $k_H/k_V$, K is also a function of $k_H/k_V$. Using the values of $G_{oH}$ in Table 4, the values of K are obtained as shown in Table 6 and FIG. 11 as a function of $r_p/r_w$ and $k_H/k_V$. For the two pretests conducted at the same measured depth, the K value can be calculated using $K_S$ and $K_T$ from Eqns. 10 and 11. Then the $k_H/k_V$ at the measured depth can be obtained by looking up Table 6 or FIG. 11 using the calculated K value and the known value of $r_p/r_w$. From knowledge of $k_H/k_V$, the horizontal and vertical permeabilities are readily determined:

$$k_H = K_T \sqrt{\frac{k_H}{k_V}}, \qquad (43)$$

$$k_V = \frac{k_H}{(k_H/k_V)}. \qquad (44)$$

TABLE 6

Numerical values of K for various values of $r_p/r_w$ and anisotropy $k_H/k_V$

| | $r_p/r_w$ = | | | | |
|---|---|---|---|---|---|
| $k_H/k_V$ | 0.025 | 0.05 | 0.1 | 0.2 | 0.3 |
| 0.01 | 1.74 | 1.74 | 1.74 | 1.82 | 1.82 |
| 0.1 | 2.48 | 2.48 | 2.53 | 2.64 | 2.69 |
| 1 | 4.08 | 4.17 | 4.26 | 4.44 | 4.65 |
| 10 | 7.96 | 8.16 | 8.49 | 8.97 | 9.37 |
| 100 | 17.94 | 18.52 | 19.51 | 20.94 | 22.10 |
| 1000 | 44.86 | 47.02 | 50.00 | 54.06 | 56.98 |
| 10000 | 120.48 | 127.39 | 136.05 | 146.52 | 153.85 |
| 100000 | 338.21 | 358.33 | 381.00 | 408.04 | 425.90 |
| 1000000 | 970.87 | 1023.02 | 1084.01 | 1152.74 | 1197.60 |

The above equations are derived based on the assumptions of a constant withdrawal rate and steady state flow. In a low permeability formation, the steady state flow condition cannot be satisfied unless a long test time is used. A constant drawdown rate is not reachable in practice because the tool needs time for acceleration and deceleration. The storage effect also makes it difficult to reach a constant rate. In an alternate embodiment of the present invention, both drawdown and buildup tests are made at substantially the same depth with the probe against a sidewall and an upper (or lower) wall. The Formation Rate Analysis (FRA) presented in U.S. Pat. No. 5,708,204 to Kasap, the contents of which are incorporated herein by reference, are used to calculate the above $K_S$ and $K_T$.

As disclosed in Kasap, pressure is measured with respect to time at a probe in hydraulic communication with the earth formation. Time derivatives of the measured pressure are determined while withdrawing fluid from the earth formation by increasing a volume of a chamber in hydraulic communication with the probe. The volume of the chamber is measured as a function of time and the time derivative of the volume is calculated. This is part of a withdrawal phase. Fluid withdrawal is stopped and the pressure buildup is measured. The permeability is calculated when the measured pressure substantially stops increasing, by determining a slope of a linear relationship of the measured pressure with respect to a fluid flow rate calculated from the time derivative of the volume and the time derivative of the pressure.

The invention has been described in terms of measurements made using logging tools conveyed on a wireline in a borehole. As noted above, The method can also be used on data obtained using measurement-while-drilling sensors on a bottomhole assembly (BHA) conveyed by a drilling tubular. Such a device is described, for example, in U.S. Pat. No. 6,640,908 to Jones et al., and in U.S. Pat. No. 6,672,386 to Krueger et al., having the same assignee as the present invention and the contents of which are fully incorporated herein by reference. The method disclosed in Krueger comprises conveying a tool into a borehole, where the borehole traverses a subterranean formation containing formation fluid under pressure. A probe is extended from the tool to the formation establishing hydraulic communication between the formation and a volume of a chamber in the tool. Fluid is withdrawn from the formation by increasing the volume of the chamber in the tool with a volume control device. Data sets are measured of the pressure of the fluid and the volume of the chamber as a function of time.

The embodiments of the invention that require making measurements on two different walls of a substantially horizontal borehole are readily accomplished in a MWD implementation. If the tests are performed after the well has been drilled, several options are available. One is to convey the pressure tester on coiled tubing. Alternatively, a downhole traction device such as that disclosed in U.S. Pat. No. 6,062,315 to Reinhardt, having the same assignee as the present invention and the contents of which are fully incorporated herein by reference, may be used to convey the pressure tester into the borehole. A traction device may also be used to withdraw the pressure tester from the borehole, or, alternatively, the withdrawal may be done using a wireline.

The processing of the measurements made by the probe in wireline applications may be done by the surface processor 21 or may be done by a downhole processor (not shown). For MWD applications, the processing may be done by a downhole processor that is part of the BHA. This downhole processing reduces the amount of data that has to be telemetered. Alternatively, some or part of the data may be telemetered to the surface. In yet another alternative, the pressure and flow measurements may be stored on a suitable memory device downhole and processed when the drillstring is tripped out of the borehole.

The operation of the probe may be controlled by the downhole processor and/or the surface processor. Implicit in the control and processing of the data is the use of a computer program implemented on a suitable machine readable medium that enables the processor to perform the control and processing. The machine readable medium may include ROMs, EPROMs, EAROMs, Flash Memories and Optical disks.

While the foregoing disclosure is directed to the specific embodiments of the invention, various modifications will be apparent to those skilled in the art. It is intended that all such variations within the scope and spirit of the appended claims be embraced by the foregoing disclosure.

What is claimed is:

1. A method of estimating permeability of an earth formation in at least one direction, the formation containing a formation fluid, the method comprising:
   (a) performing a first flow test with a probe in a first direction against a wall of a borehole in the earth formation, the borehole having an axis that is inclined to a direction of minimum permeability of the earth formation;
   (b) performing a second flow test with the probe in a second direction against the wall of the borehole, the first and second directions not being on opposite sides of the borehole; and
   (c) estimating a permeability from analysis of the first flow test and the second flow test.

2. The method of claim 1 wherein the permeability is estimated in two orthogonal directions.

3. The method of claim 1 wherein performing the first flow test and the second flow test further comprises using a probe having a substantially circular aperture.

4. The method of claim 1 wherein performing the first flow test and the second flow test further comprises withdrawing fluid from the earth formation and monitoring a pressure of the formation during the withdrawal.

5. The method of claim 1 wherein at least one of the first flow test and the second flow test further comprises a drawdown and a pressure buildup.

6. The method of claim 1 wherein the borehole has an axis that is substantially parallel to a direction of maximum permeability of the formation.

7. The method of claim 6 wherein estimating the permeability further comprises:
   (i) estimating a quantity related to horizontal permeability from the first flow test, and
   (ii) estimating a quantity related to horizontal and vertical permeability from the second flow test.

8. The method of claim 7 further comprising using relations of the form:

$$K_S \equiv G_{oH} k_H = \frac{q_S \mu}{r_p(p_i - p_{p,S})} \text{ and}$$

$$K_T \equiv \sqrt{k_H k_V} = \frac{q_T \mu}{4 r_p(p_i - p_{p,T})}$$

where:
  $k_H$ is the horizontal permeability,
  $k_V$ is the vertical permeability
  $q_S$ is a flow rate in the first flow test,
  $q_T$ is a flow rate in the second flow test,
  $\mu$ is a viscosity of the formation fluid,
  $r_p$ is a radius of a probe used in the first pressure test and the second pressure test,
  $p_i$, is an initial formation fluid pressure in the first pressure test and the second pressure test,
  $p_{pS}$ is a fluid pressure corresponding to $q_S$ in the first pressure test, and
  $P_{pT}$ is a fluid pressure corresponding to $q_r$ in the second pressure test.

9. The method of claim 1 further comprising transporting a probe used for making the first flow test and the second flow test on at least one of (i) a wireline, (ii) a drillstring, (iii) coiled tubing, and, (iv) a traction device.

10. The method of claim 1 wherein estimating the permeability in at least one of two different directions further comprises using at least one of (i) a downhole processor, and, (ii) a surface processor.

11. The method of claim 1 further comprising performing the first flow test at a depth substantially equal to a depth at which the second flow test is performed.

12. An apparatus for estimating permeability of an earth formation in at least one direction, the formation containing a formation fluid, the apparatus comprising:
   (a) a probe conveyed in a borehole in the earth formation, the probe configured to make making fluid flow tests in the borehole, the borehole having an axis that is inclined to a direction of minimum permeability of the earth formation;
   (b) a processor configured to estimate a permeability in the at least one direction from analysis of flow tests made by the probe in a plurality of different directions against the wall of the borehole, at least two of the directions not being on opposite sides of the borehole.

13. The apparatus of claim 12 wherein the borehole has an axis that is substantially parallel to a direction of maximum permeability of the earth formation.

14. The apparatus of claim 12 wherein the probe is in hydraulic communication with the formation fluid.

15. The apparatus of claim 12 wherein the processor estimates the permeability in two orthogonal directions.

16. The apparatus of claim 12 wherein the probe has a substantially circular aperture.

17. The apparatus of claim 12 further comprising a flow rate sensor configured to measure a flow rate in the probe, and a pressure sensor which measures a pressure of the formation during at least one flow test.

18. The apparatus of claim 12 wherein at least one of the flow tests comprises a drawdown.

19. The apparatus of claim 12 wherein at least one of the flow tests comprises a drawdown and a pressure buildup.

20. The apparatus of claim 12 wherein the processor is configured to estimate the permeability in at least one of two directions by further:
   (i) estimating a quantity related to horizontal permeability from a first flow test, and
   (ii) estimating a quantity related to horizontal and vertical permeability from a second flow test.

21. The apparatus of claim 12 further comprising a conveyance device configured the probe in the borehole, the conveyance device being selected from the group consisting of (i) a wireline, (ii) a drillstring, (iii) coiled tubing, and, (iv) a traction device.

22. The apparatus of claim 12 wherein the processor is at a location selected from (i) a downhole location, and, (ii) a surface location.

23. A machine readable medium for use with a probe conveyed in a borehole in the earth formation, the borehole having an axis inclined to a direction of minimum permeability of the earth formation, the probe configured to perform a plurality of flow tests against the wall of the borehole, the medium containing instructions which enable a processor to:
   (a) estimate a permeability of the earth formation in at least one direction from analysis of the flow tests made by the probe in two different directions against the wall of the borehole.

24. The machine readable medium of claim 23 wherein the instructions further enable the processor to estimate the permeability in two orthogonal directions.

25. The machine readable medium of claim 23 wherein the instructions further enable the processor to monitor:
   (A) an output of a flow rate sensor which measures a flow rate into the probe, and
   (B) an output of a pressure sensor which measures a pressure of the formation.

26. The machine readable medium of claim 23 wherein the instructions further enable the processor to control the probe to perform a drawdown and a pressure buildup.

27. The medium of claim 23 wherein the borehole has an axis that is substantially parallel to a direction of maximum permeability of the earth formation.

* * * * *